(12) United States Patent
Short

(10) Patent No.: US 10,638,835 B1
(45) Date of Patent: May 5, 2020

(54) OVERBED TABLE AND TRANSPORT CHAIR

(71) Applicant: J. Gordon Short, Salt Lake City, UT (US)

(72) Inventor: J. Gordon Short, Salt Lake City, UT (US)

( * ) Notice: Subject to any disclaimer, the term of this patent is extended or adjusted under 35 U.S.C. 154(b) by 37 days.

(21) Appl. No.: 16/217,810

(22) Filed: Dec. 12, 2018

(51) Int. Cl.
| *A61G 7/08* | (2006.01) |
| *A47C 13/00* | (2006.01) |
| *A47B 85/04* | (2006.01) |
| *A47B 23/06* | (2006.01) |
| *A47B 23/04* | (2006.01) |
| *A61G 7/10* | (2006.01) |
| *A47B 21/06* | (2006.01) |
| *A47B 21/02* | (2006.01) |

(52) U.S. Cl.
CPC .............. *A47B 85/04* (2013.01); *A47B 21/02* (2013.01); *A47B 21/06* (2013.01); *A47B 23/046* (2013.01); *A47B 23/06* (2013.01); *A61G 7/1019* (2013.01); *A61G 7/1046* (2013.01); *A61G 7/1059* (2013.01); *A61G 7/1073* (2013.01); *A47B 2021/066* (2013.01); *A47B 2023/047* (2013.01)

(58) Field of Classification Search
CPC .. A61G 7/0503; A61G 5/1059; A61G 12/001; A61G 12/008; A47B 85/04
See application file for complete search history.

(56) References Cited

U.S. PATENT DOCUMENTS

| 5,551,105 | A  | * | 9/1996  | Short ................... A61G 5/1059 |
|           |    |   |         |                             280/250.1 |
| 6,231,067 | B1 | * | 5/2001  | Johnson ................... A61G 5/14 |
|           |    |   |         |                              180/65.1 |
| 6,705,239 | B2 | * | 3/2004  | Doyle ...................... A47B 9/04 |
|           |    |   |         |                               108/147 |
| 7,275,907 | B1 | * | 10/2007 | Reichard ............... B60P 3/1033 |
|           |    |   |         |                               114/344 |
| 7,716,759 | B2 | * | 5/2010  | Wilder ................. A61G 7/1011 |
|           |    |   |         |                              280/47.41 |
| 8,840,175 | B2 | * | 9/2014  | Short ..................... A47B 85/04 |
|           |    |   |         |                               297/119 |
| 9,367,061 | B2 | * | 6/2016  | Miller .................. G05B 19/042 |
| 9,624,077 | B1 | * | 4/2017  | Jordan ...................... B66F 3/46 |
| D787,073  | S  | * | 5/2017  | Livengood .................... D24/185 |
| 9,844,871 | B2 | * | 12/2017 | Goodwin .................. B25J 11/008 |
| 9,919,625 | B1 | * | 3/2018  | Barbier .................... A47C 7/628 |
| 9,993,076 | B2 | * | 6/2018  | Harrington .......... A47B 23/043 |
| 10,051,960| B1 | * | 8/2018  | Siebert ................... A47B 85/04 |
| 10,130,536| B2 | * | 11/2018 | Roussy .................. A61G 7/002 |
| 10,582,981| B2 | * | 3/2020  | Childs ..................... A61B 90/50 |
| 2009/0314923 | A1 | * | 12/2009 | Timoszyk ........... A61M 5/1415 |
|           |    |   |         |                               248/647 |
| 2014/0239680 | A1 | * | 8/2014 | Short ..................... A47B 85/04 |
|           |    |   |         |                              297/183.6 |
| 2020/0077788 | A1 | * | 3/2020 | Albers ..................... A47B 9/12 |

* cited by examiner

*Primary Examiner* — Shin H Kim
(74) *Attorney, Agent, or Firm* — J. Todd Rushton

(57) ABSTRACT

The present invention is an overbed table and transport chair, or more specifically, the present invention is a medical furnishing that serves as an adjustable overbed table in a first configuration and a wheeled transport chair in a second configuration. The present invention may also serve as a medical staff work station, provide storage of patient records and medical charts, storage for the patient's personal effects, personal mirror, IV stand, catheter bag stand, and secure storage for portable oxygen.

9 Claims, 11 Drawing Sheets

OVERBED TABLE AND TRANSPORT CHAIR

The present application relates directly to U.S. Pat. No. 8,840,175, CONVERTIBLE MULTIFUNCTION OVERBED TABLE AND CHAIR, by J. Gordon Short, filed Feb. 26, 2013; the disclosure therein incorporated by reference.

BACKGROUND

A multi-function patient support apparatus such as the overbed table and transport chair of the present invention has the potential to solve myriad problems associated with space restrictions in most hospital, rehabilitation and convalescence centers and also the high cost of fully stocking a facility with the proper patient support equipment for each individual room. The inventor has previously addressed these issues with prior embodiments of the present invention including an embodiment entitled APPARATUS COMBINING OVERBED TABLE, IV STAND, WALKER AND SEAT, issued as U.S. Pat. No. 5,551,105, filed Aug. 26, 1994 and the above reference embodiment for a CONVERTIBLE MULTIFUNCTION OVERBED TABLE AND CHAIR. The inventor recognized the benefits of the prior embodiments; however, he also acknowledges certain limitations with the most recent embodiment that substantially affect utility and also a potential the patient safety issue. The most significant limitation is the unnecessarily cumbersome rotational track mechanism when changing the configuration between the overbed table and the seat function. However, the most significant issue is the potential for a patient to become trapped or pinned under the overbed table in the event the patient bed is raised beyond the set height of the overbed table.

What is needed is an improved overbed table and transport chair which will allows for simple configuration changes between the overbed table function and transport chair and the overbed table to provide relief in the event that a patient bed is inadvertently raised above the set height of the overbed table.

SUMMARY OF THE INVENTION

The present invention relates to an overbed table and transport chair, more specifically, the present invention relates to a multifunction patient support apparatus, that may be used as an overbed table, a patient transport chair, supplemental guest seating, provide storage for the patient's personal effects, provide organization of the patient's medical charts, securely store a supplemental oxygen bottle, and provide an elevated stand for intravenous fluids.

A first embodiment of the present invention, or overbed table and transport chair, has a wheeled base portion with upright supports and a rotatable overbed table and transport chair portion. The wheeled base has a low profile to extend under a patient's bed; a width somewhat wider than the table/chair portion and extends away from the upright supports to create a stable base for the device. The wheels are a caster arrangement that allows for easy multi-directional movement when the present invention is configured as an overbed table. Front casters are tandem sets on each side configured to allow the apparatus to easily move over the threshold gap between an elevator floor and the adjacent landing, or over imperfections in the concrete or asphalt of a patient loading area. The rear casters can be locked into a position parallel with the length of the base portion to allow improved steering control when the apparatus is configured into a transport chair. The rear casters also incorporate a rolling lock feature in order to prevent the overbed table or transport chair from moving once placed in a desired position.

When the device is configured as an overbed table, the overbed table includes a horizontal support surface that can accommodate a food tray and other patient personal care items. In one embodiment, the horizontal surface includes a raised edge to contain items that may be predisposed to roll on a flat surface and contain any spilled liquids. One embodiment of the overbed table includes one or more storage compartments toward the supported end of the table. The storage compartments including a hinged cover to secure items in the compartments when the overbed table is moved into a transport chair position. The storage compartments are provided as a convenience, allowing the patient to store items such as books, writing material, personal hygiene items, wallet, keys and cell phone.

The height of the table is infinitely adjustable within an operable range using a 12 volt DC actuator mechanism. In one embodiment the actuator mechanism is screw type actuator, having a DC motor, drive gear and threaded ram assembly having a stabilizing frame including a roller slide frame and a contact pad which rests on the free end of the threaded ram. The contact pad is configured to engage with the attached end of the seat/table or engage the seat/table proximate the hinge when the device is configured as an overbed table. This configuration allows the overbed table to release freely upward if a patient bed is inadvertently raised above the set height of the overbed table; preventing the patient from being entrapped between the overbed table and the bed. The actuator mechanism can be powered directly using a transformed 120 AC power source or by using a rechargeable 12 volt DC lithium ion battery integrated into the rolling base assembly.

One embodiment of the overbed table includes an anti-rotate assembly configured to prevent the overbed table from inadvertently being elevated from the free end and causing items on the table from being displaced or liquids being be spilled. The anti-rotate assemble including a t-bolt attached to the front surface of the seat support platform and a t-bolt slot formed in the bottom surface of the seat portion of the overtable/transport chair. When the transport chair is in its lowest position it can be rotated into the overbed table position, the t-bolt on the seat support platform will insert into an entry point of the t-bolt slot and the t-bolt is retained within the slot as the overbed table is elevated. In another embodiment of the present invention, the t-bolt slot will have an exit opening at the lowest point of the slot or when the overbed table is raised beyond normal operating range, this allows the overbed table to tilt away in the event the overbed table is raised beyond the stroke of the actuator mechanism.

One embodiment of the present invention is convertible from an overbed table to a transport chair configuration by simply lowering the overbed table into the lowest position and raising the free end of the overbed table and rotating the hinged end approximately 100 degrees until the underside of the seat rests on the seat support platform formed in the center of the rolling frame. The seat support platform includes a seat lock mechanism that prevents the seat from tipping forward. A catch bar attached to the base of the seat is pushed over a ramped portion of a spring loaded latch causing the handle of the latch to pivot up and allow the catch bar to move into the mouth of a catch slot or hook formed in the retaining end of the latch. Once the catch bar has passed the ramp portion of the latch, the spring is biased to move the handle down and retain the catch bar in the catch slot. Releasing the seat is accomplished by raising the latch handle.

The transport chair is configured having the front of the seat 22 inches (55.9 cm) above the floor which provides a slightly increase height allowing most patients to rise to a standing position more easily. The transport chair includes foot rest formed in the rolling frame above the front casters, the foot rests are a standard 18 inches (45.7 cm) below the front lip of the seat. Armrests formed in the rolling frame uprights are configured to rotate out or pull down in order to provide the patient arm support and improved comfort and stability, or to be moved up out of the way if it is desired to slide a patient sideways out of the chair and onto another surface having a similar height such as moving a patient from the chair and onto the top of a bed.

In one embodiment, the underside surface of the table forms the seat back and slopes backward approximately 3 to 10 degrees from an upright position. The seat bottom is configured to slope from front to back about 3 degrees. In other embodiments, the degree of incline for the seat back and bottom are set at different angles to improve user comfort and safety. In yet other embodiments, the degree of incline for the seat back and bottom are adjustable.

Additional convenience features will be included in one embodiment of the present invention or overbed table and transport chair. These features include but are not limited to push handles and extendable IV bag hangers formed in the back portion of the rolling frame uprights, a 120 volt AC outlet with USB power outlet is also recessed into one or both of the vertical uprights. An oxygen bottle holder is formed into the back of the seat support platform. Provision to hang a Foley bag is provided in the front lip of the seat. A storage basin is formed in the bottom of the rolling frame.

The assembly is ergonomically contoured plastic that can be easily cleaned and disinfected. In another embodiment, the bulk of the components for the entire assembly may be fabricated using plastics and other materials having antibacterial properties. It is contemplated the larger components of present invention may be fabricated using methods such as rotary molding or laid up using a last or molds as required. Materials may be a plastic or composite material, such as, fiberglass, carbon fiber, Kevlar® or similar materials know or yet to be developed. The device of the present invention could also be constructed as a metal skeleton and plastic or metal skin.

BRIEF DESCRIPTION OF THE DRAWINGS

The following description of the embodiments can be understood in light of the Figures, which illustrate specific aspects of the embodiments and are part of the specification. Together with the following description, the Figures demonstrate and explain the principles of the embodiments. In the Figures the physical dimensions of the embodiment may be exaggerated for clarity. The same reference numerals in different drawings represent the same element, and thus their descriptions may be omitted.

DETAILED DESCRIPTION OF THE DRAWINGS

Figure 1:
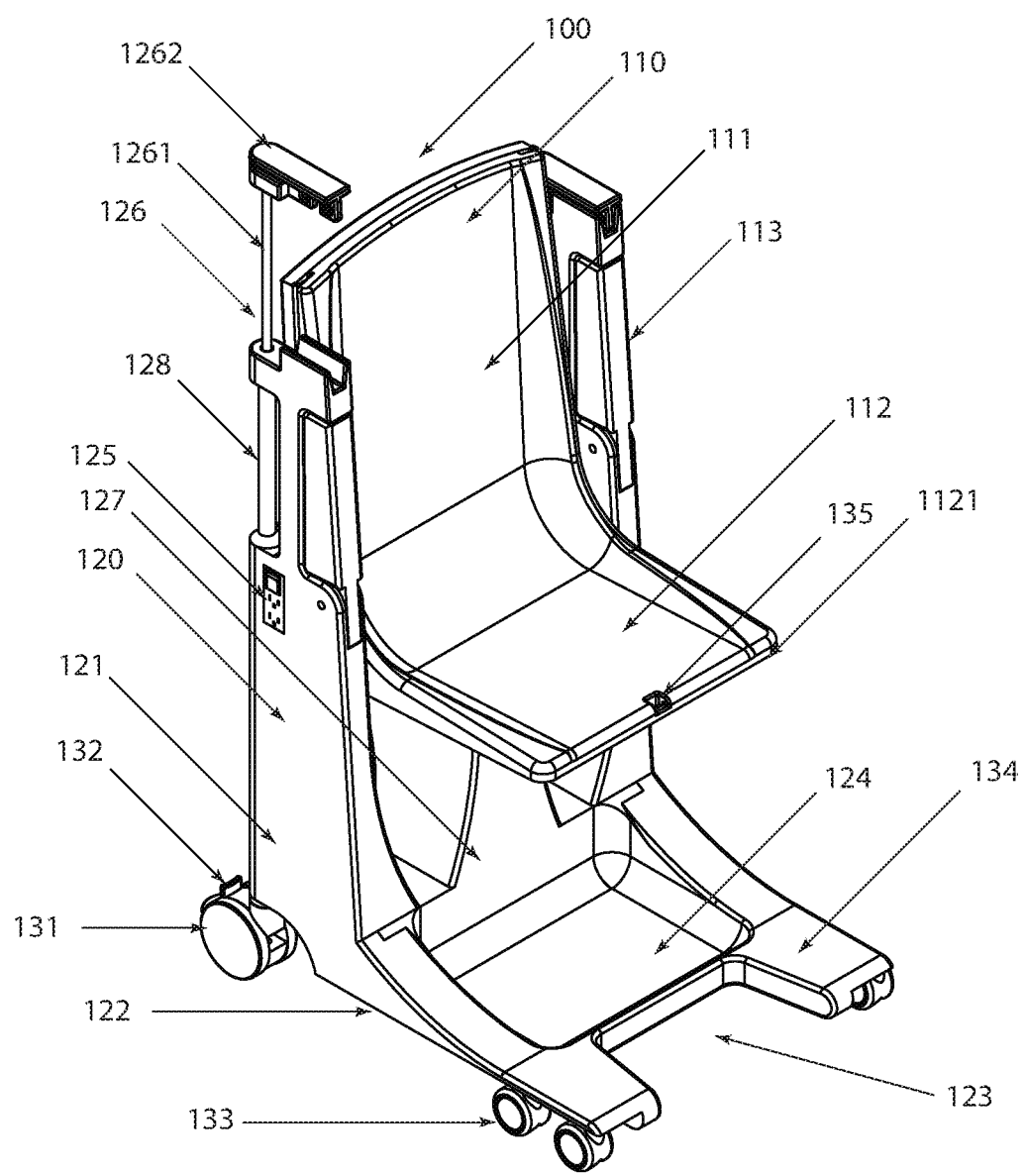
FIG. 1 is a front perspective view of the present invention configured as a transport chair.
Figure 2:
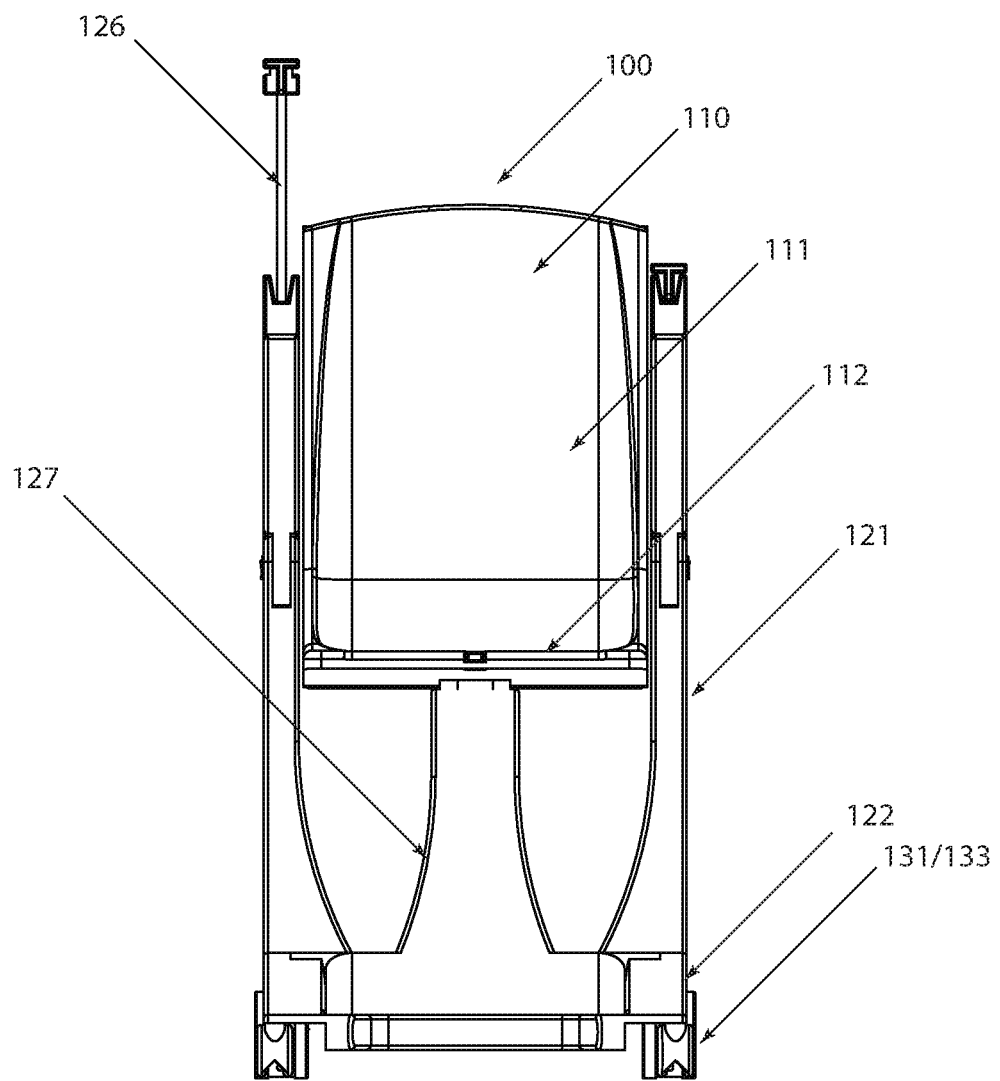
FIG. 2 is a front view of the present invention configured as a transport chair.
Figure 3:
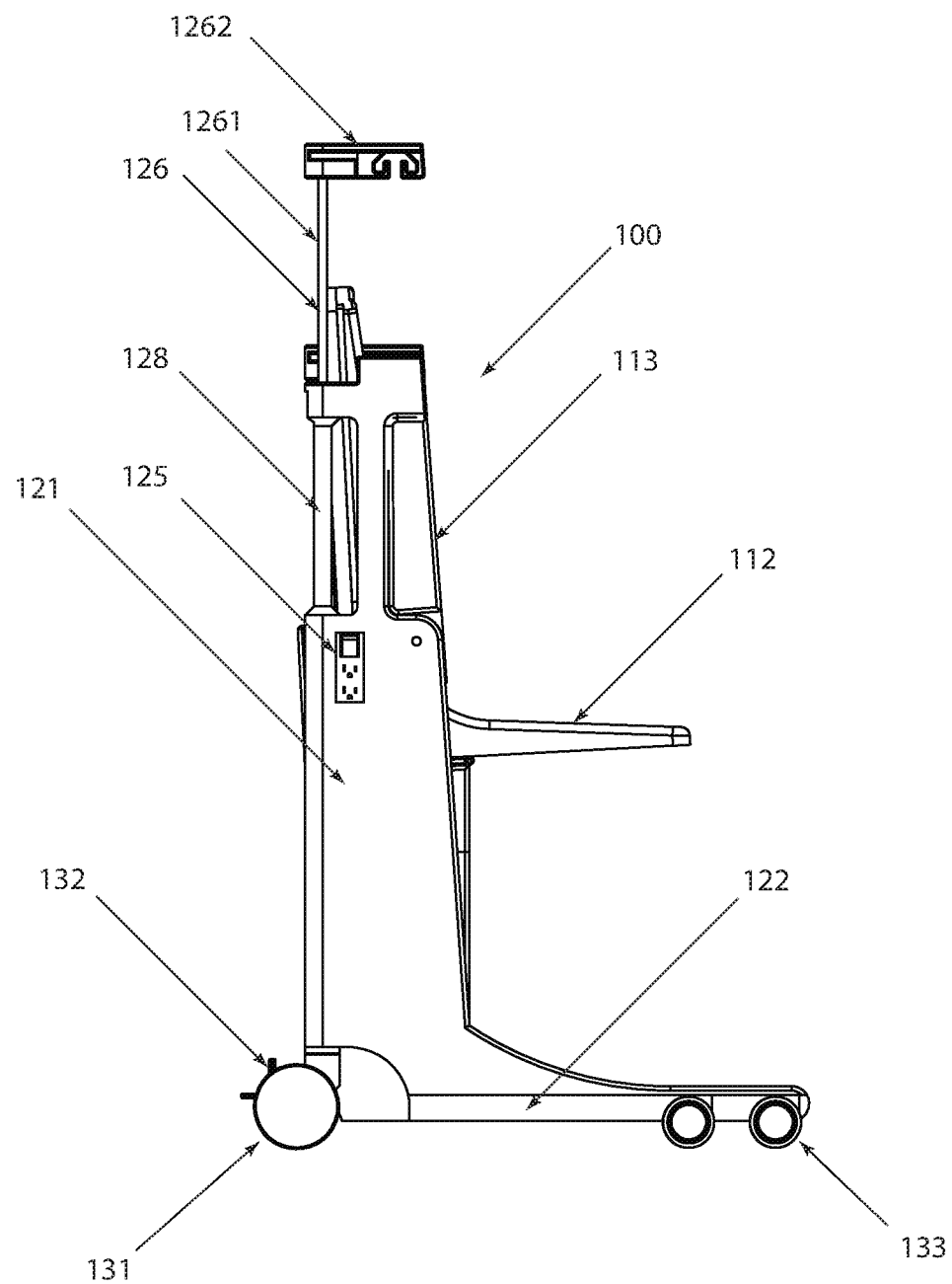
FIG. 3 is a side view of the present invention configured as a transport chair.

For the purposes of promoting an understanding of the principles in accordance with the disclosure, reference will be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

As used in this specification and the appended claims, the singular forms "a," "an," and "the" include plural referents unless the context clearly dictates otherwise. In describing and claiming the present disclosure, the following terminology will be used in accordance with definitions set out below. As used herein, the terms "comprising," "including," "containing," "characterized by," and the grammatical equivalents thereof are inclusive or open-ended terms that do not exclude additional, unrecited elements or method processes. A number used to represent a feature of the present invention may be repeated throughout the series of drawings and represents the same feature in each figure.

A first embodiment of the present invention or overbed table and transport chair 100 configured as a transport chair is shown in FIGS. 1 through 4. The overbed table and transport chair 100 including a seat 110, having a seat back 111, a seat base 112 extending away from the seat back 111 forming substantially an "L" shape, and armrests 113 configured to provide comfortable support for a patient while in sitting position whether in a patient room or while being moved within the hospital or rehabilitation facility environment. The armrests 113 are folding allowing for additional seat width clearance and allow a patient to transfer laterally from the seat 111 to another surface such as the patient bed.

The overbed table and transport chair 100 is supported using a rolling frame 120 including, opposing vertical upright members 121, and a substantially rectangular rolling support base 122. The support base 122 including rear casters 131 at the rear of the base proximately under the vertical upright members 121, the rear casters 131 including foot controls 132 configures to provide a rolling lock, when it is desirable to park the overbed table and transport chair 100 in a fixed position, and a pivot lock to align the rolling direction of the rear casters 131 parallel with the length of the rolling support base 122. The pivot lock position provides improved steering and control when moving the overbed table and transport chair 100 over distance. Tandem front casters 133 are attached under the front corners of the rolling support base 122, the tandem front casters 133 provide a reduced ground pressure or point load under each caster and allows a smaller wheel diameter caster 133 to move over imperfections in the rolling surface, such as, sidewalk seams, door thresholds and the gap between a landing floor and an elevator floor with ease.

The rolling frame 120 including a base cutout 123 in front portion of the support base 122, the base cutout 123 allows a patient's legs and feet to extend vertically from the front edge 1121 of the seat base 112 directly to the floor. The base cutout 123 enables the patient to stand next to the front the seat base 112 when sitting and allow the patient to rise comfortably from a sitting position. Foot rests 134 are formed outside of the base cutout 123 directly over the tandem front casters 133; the foot rests 134 allow the patient to elevate their feet and remove pressure from the bottom of their thighs when they are sitting for an extended period of time and prevent the patient's feet from dragging when using the device of the present invention as a transport chair. The rolling frame 120 also includes myriad convenience features such as base storage bin 124 formed in the rear portion of the rolling base 122, the storage bin 124 is available to store personal items such as a hand bag, purse or suitcase when transporting a patient. An 120 v AC electrical/USB outlet 125 may be attached to or recessed into the vertical upright members 121; this feature provides easily accessible power for the patient when using items, such as, a laptop computer, tablet PC or when charging a personal cell phone, speaker, camera or to provide a power source for an IV infusion pump. Push handles 128 are formed in the top of the vertical upright members 121, allowing a nurse or orderly to comfortably push or maneuver the device 100 or the device 100 and patient when used as a transport chair. One or more retractable IV stands 126 are formed in the top portion of the vertical upright members 121 with the extension pole 1261 of the IV stand running through the push handles 128. The IV stand 126 having a top cantilevered portion 1262 which forms the top surface of the upright member 121, the free end of the cantilevered portion 1262 having an IV bag hook 1263 allowing for the convenient suspension of an IV fluid bag. The IV stands 126 can be used for the patient during transport or for general use when the patient is convalescing in bed. A Foley catheter bag receptacle 135 is formed in the front edge 1121 of the seat base 112.

The support base 122 includes a seat support platform and overbed table height adjustment housing 127 formed between the two vertical support members 121. An oxygen bottle holder 129 incorporated into the back surface of the seat support platform and overbed table height adjustment housing 127.

Figure 4:
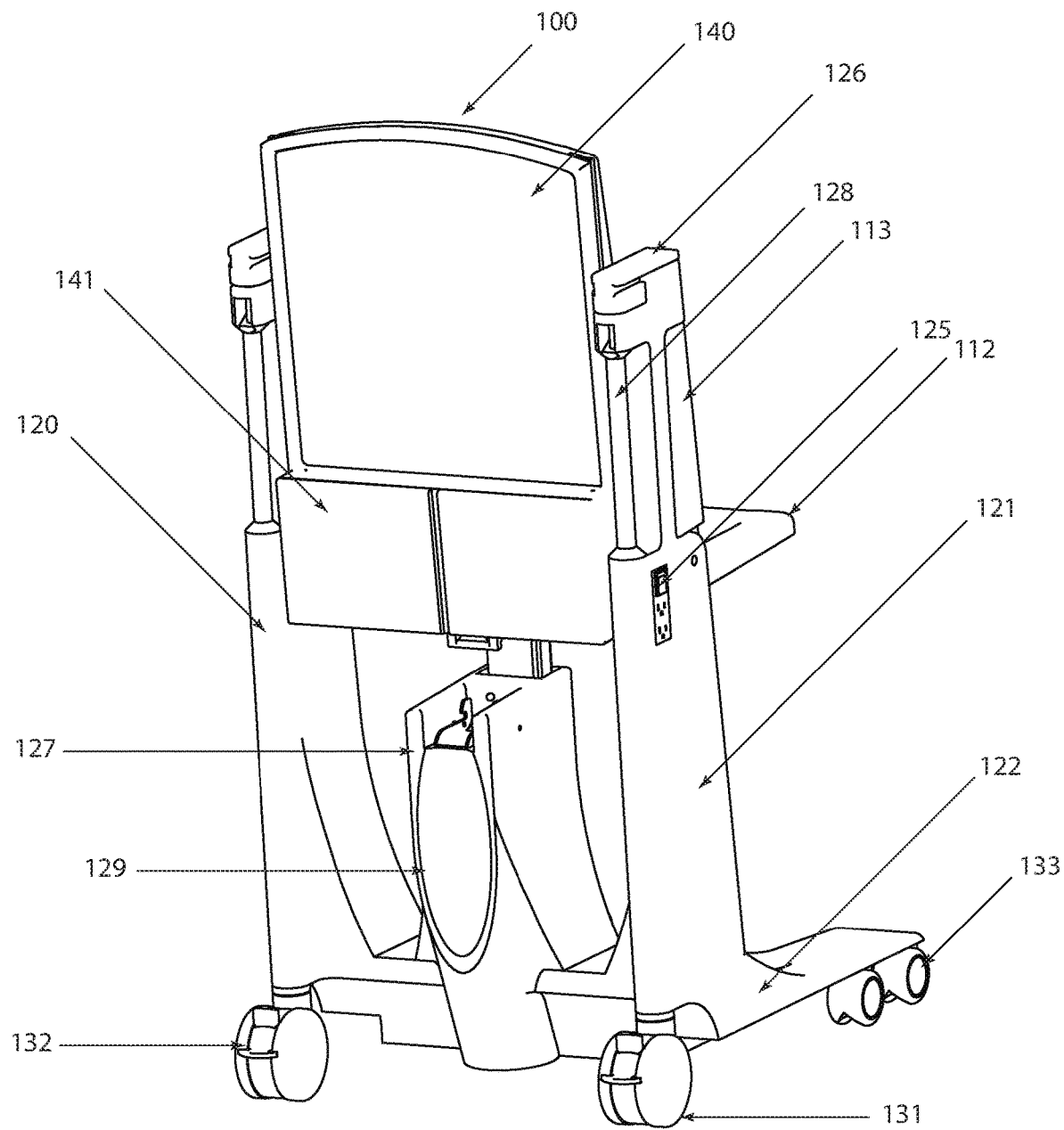
FIG. 4 is a back perspective view of the present invention configured as a transport chair.

FIG. 4 clearly shows the position of the overbed table 140 and the table storage when the overbed table and transport chair 100 is configured as a transport chair.

Figure 5:
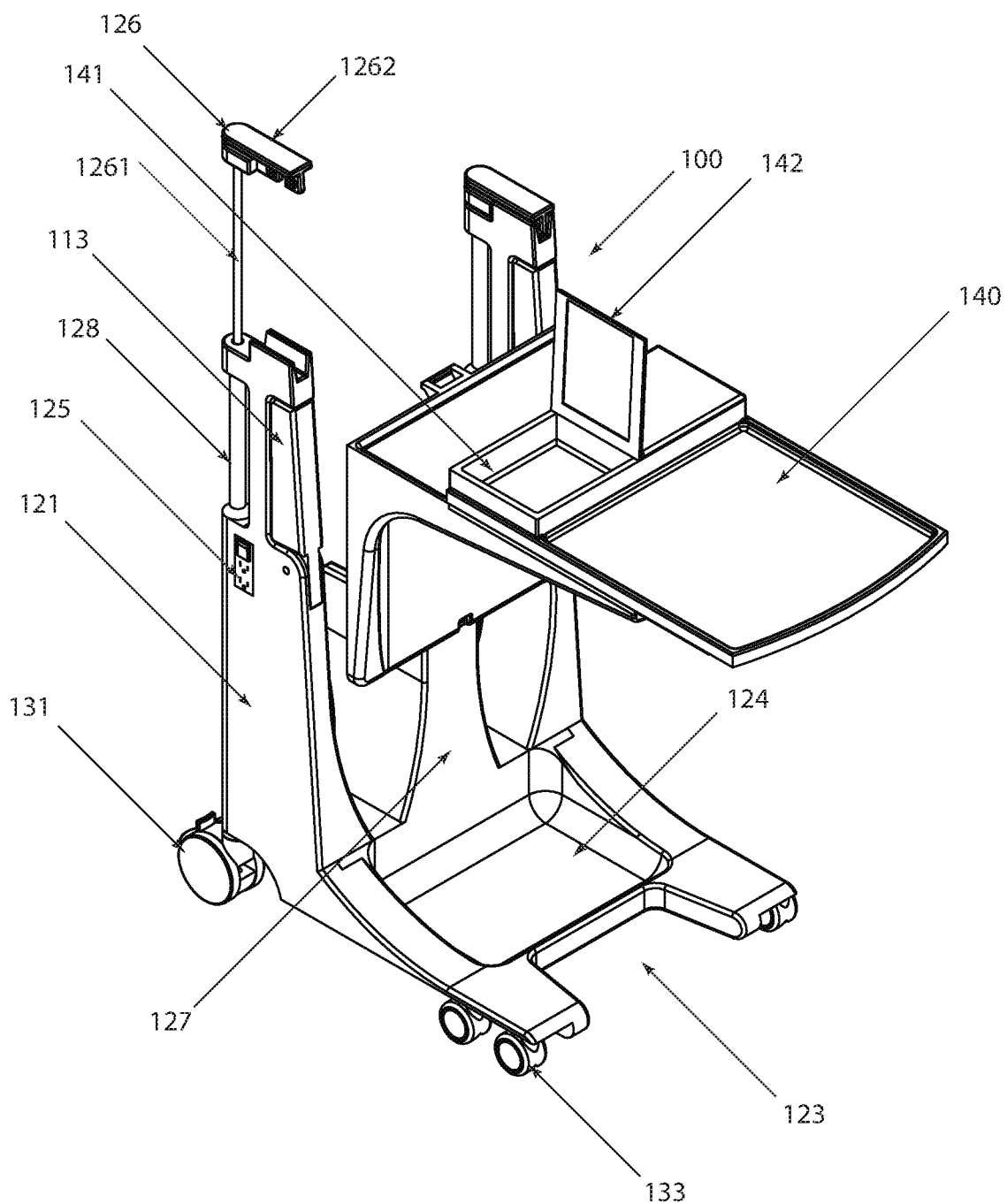
FIG. 5 is a perspective view of the present invention configured as an overbed table.
Figure 6:
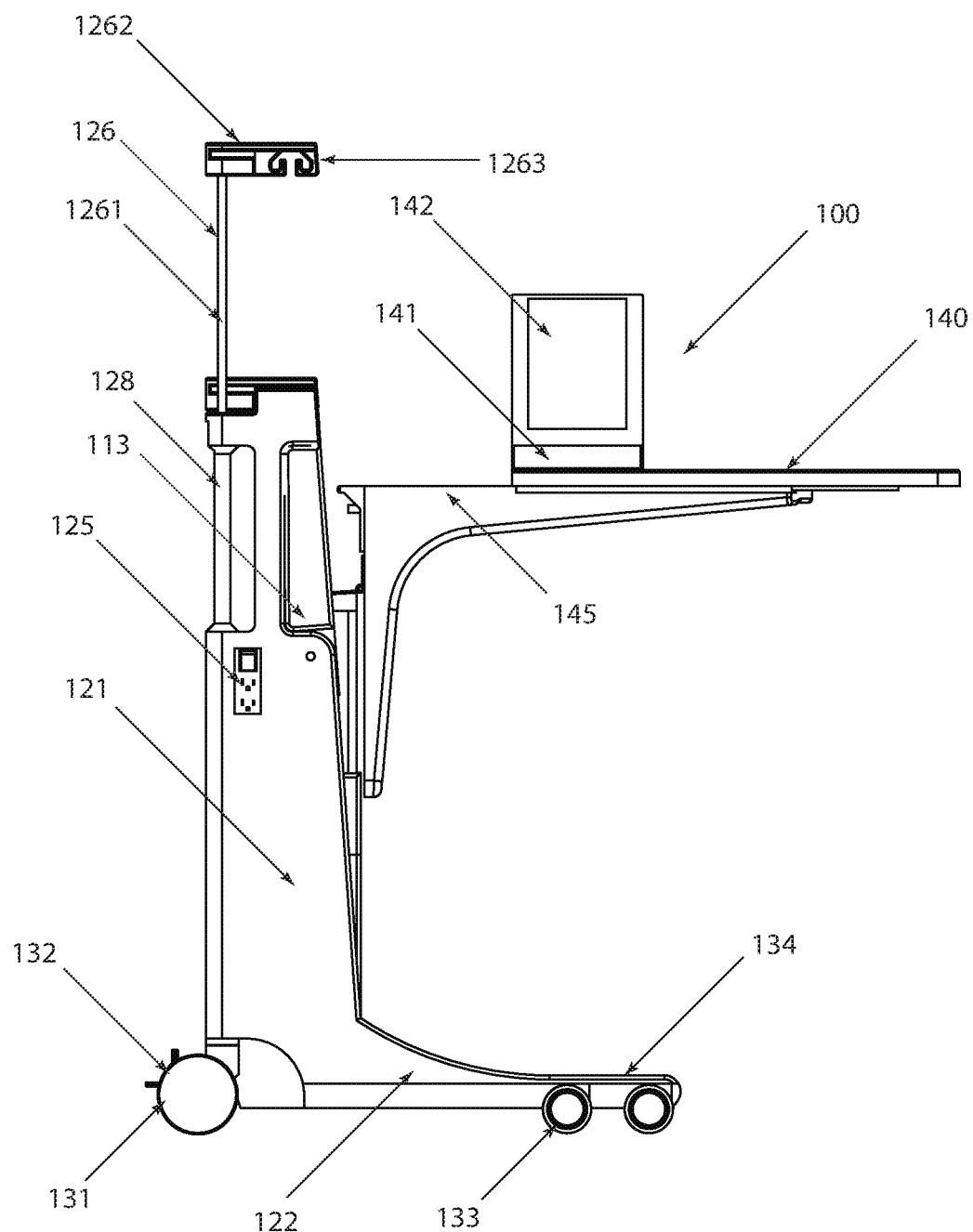
FIG. 6 is a side view of the present invention configured as an overbed table in a raised position.
Figure 7:
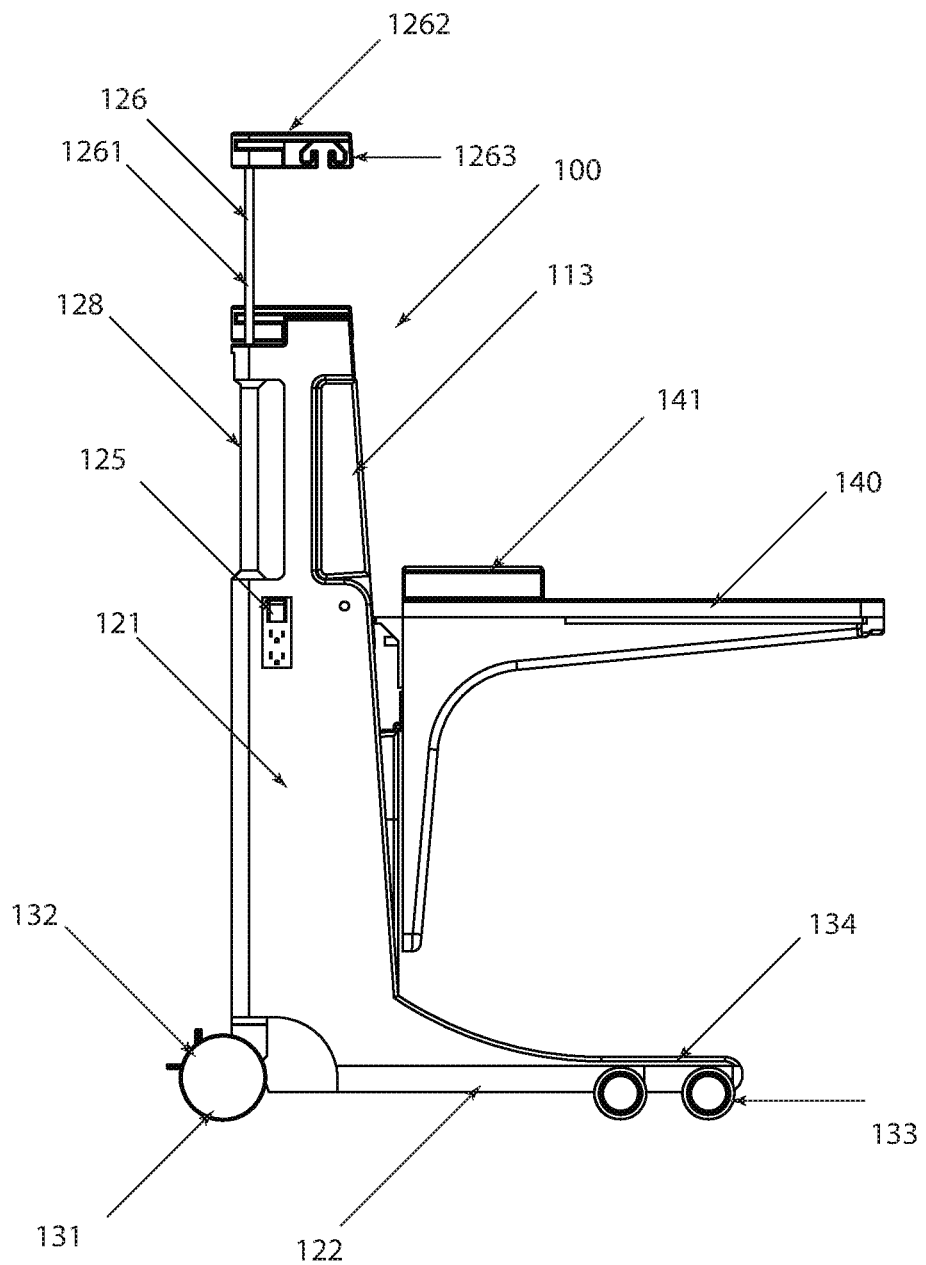
FIG. 7 is a side view of the present invention configured as an overbed table in a lowered position.

FIGS. 5 through 7 show the device of the present invention or overbed table and transport chair 100 configured as an overbed table, including an overbed table top 140. The table top 140 includes one or more storage compartments 141 having locking covers 142, the underside of the covers 142 may include mirrors. The table top 140 having a sliding mechanism 145 allowing the patient to extend the table top 140 more fully over their body or to retract the table top 140 away without moving or rolling the entire overbed table and transport chair assembly 100. The height of the overbed table top 140 is infinitely adjustable between a high position as shown in FIG. 6 and a low position depicted in FIG. 7.

Figure 8A:
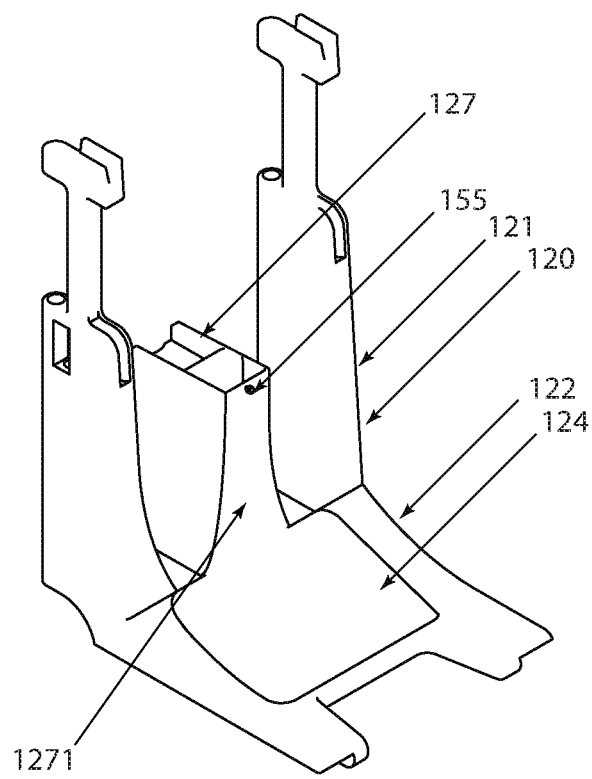
FIG. 8A is a perspective view of the base assembly.
Figure 8B:
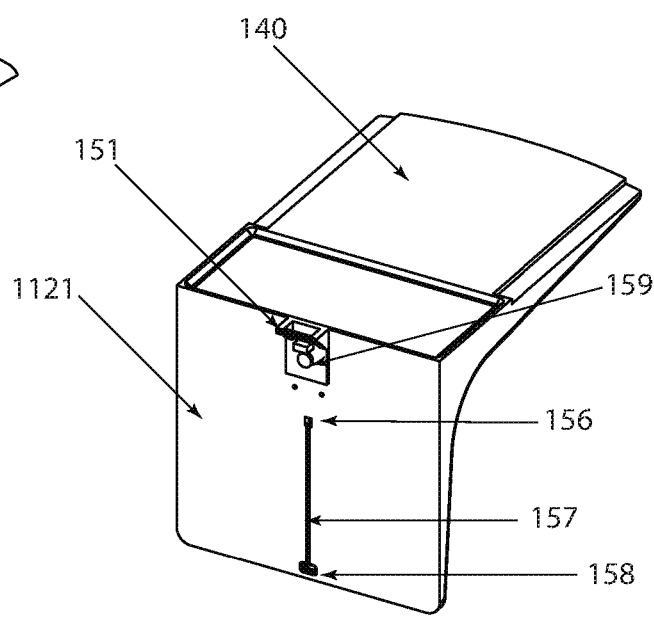
FIG. 8B is a perspective view of the overbed table/transport chair assembly.

FIGS. 8A and 8B is shown in order to understand the operation of the anti-rotate mechanism of the present invention. FIG. 8A is a perspective view of the base assembly 120 having a base portion 122, with storage bin 124 and vertical upright supports 121. The seat support platform 127 is positioned between the upright supports 121 and includes an anti-rotate t-bolt 155 attached to the front surface 1271 of the seat support platform 127. A perspective view of the overbed table 140 is depicted in FIG. 8B. The overbed table 140 including the seat catch bar 151, an actuator micro-switch 159 and a t-bolt slot 157 formed in the underside of the seat portion 1121. The t-bolt slot having a slot opening 156 at the upper end of the slot 157 and an exit tilt opening 158 formed at the bottom portion of the t-bolt slot 157. When overbed table/transport chair is converted into an overbed table, the actuator must be in its lowest position, and the transport chair 110 can be rotated into the overbed table 140 position, the t-bolt 155 on the front surface 1271 of the seat support platform 127 will insert into an entry opening 156 of the t-bolt slot 157 and the t-bolt 155 is retained within the slot 157 as the overbed table is elevated. The t-bolt slot 157 may also have an exit opening 158 at the lowest point of the slot 157 or when the overbed table 140 is raised beyond the normal operating range, this allows the overbed table 140 to slide away in the event the overbed table 140 is inadvertently raised beyond the stroke of the actuator mechanism. The actuator micro-switch 159 configured to prevent the lift mechanism from operating when the overbed table/transport chair 100 is in the transport chair configuration.

Figure 9A:
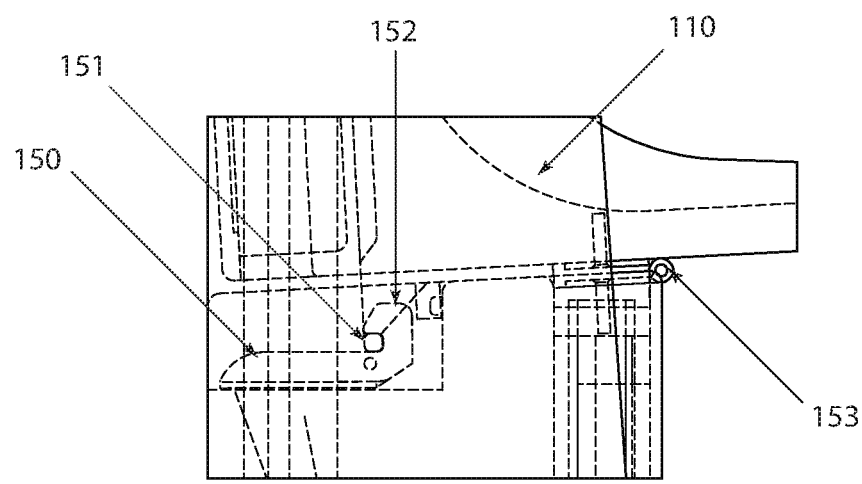
FIGS. 9A and 9B are detail views of the transport chair lock mechanism of the present invention.
Figure 9B:
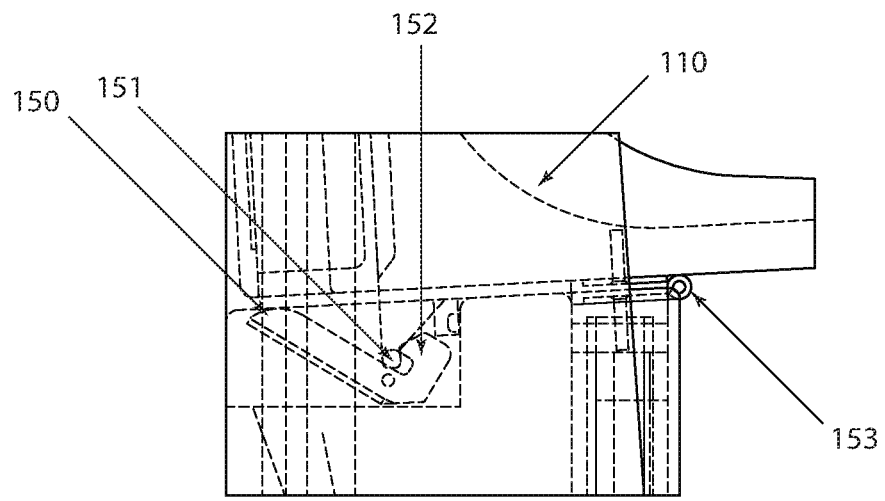

One embodiment of the present invention, shown in FIGS. 9a and 9b, including a seat latch 150 configured to secure the seat 110 of the overbed table and transport chair 100 in the transport position. The seat latch 150 including a latch hook 152 and catch bar 151. The seat latch 150 biased in a closed/locked position over the catch bar 151 by a torsion spring (not shown). The seat base 110 is configured to pivot on the seat support platform and overbed table height adjustment housing 127 using a pin and barrel hinge assembly 153. The seat latch 150 configured to lock automatically when the seat assembly 110 is moved into the transport chair configuration. In order to release the seat base and move the assembly to the overbed table 140 configuration the user must raise the free end of the seat latch 150 and disengage the hook portion 152 of the seat latch 150 from around the catch bar 151.

Figure 10A:
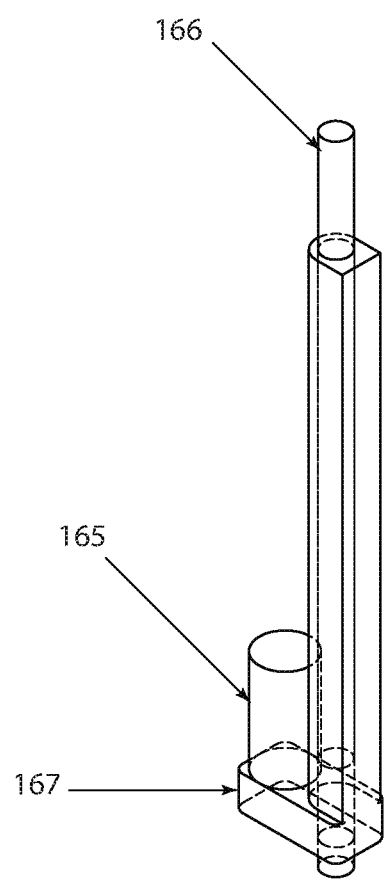
FIG. 10A is a perspective view of the overbed table lift mechanism of the present invention.
Figure 10B:
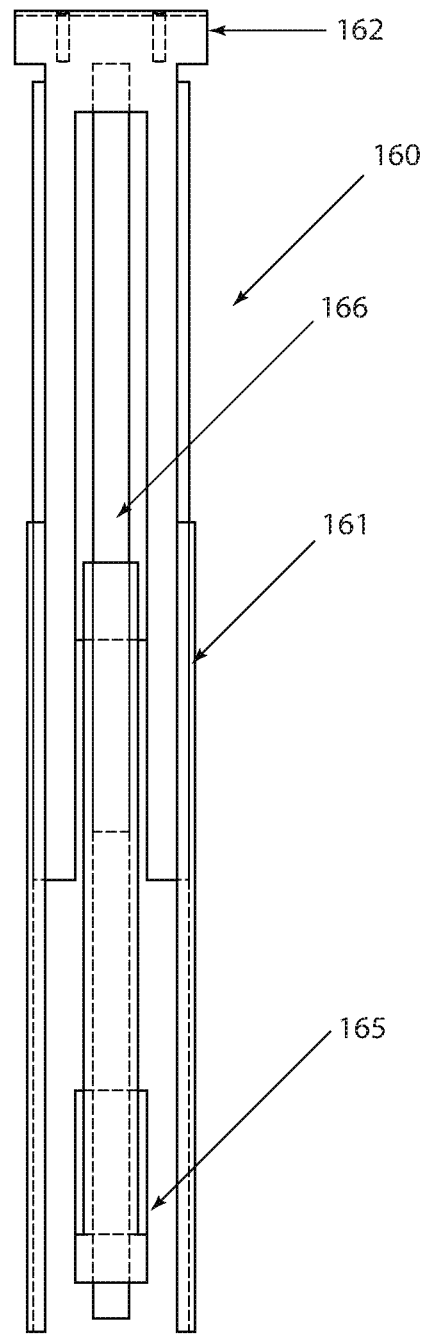
FIG. 10B is front view of the overbed table lift mechanism and roller slide frame assembly of the present invention.

FIGS. 10a and 10b depict the screw lift actuator mechanism 160 installed in the seat support platform and overbed table height adjustment housing 127. The lift actuator mechanism including a roller frame 161 configured to provide smooth height adjustments with improved stability and a resistance to twisting or flexure. The roller frame 161 including opposing guide rails and mating telescoping extension rails having a plurality of ball bearings displaced between the guide rails and the telescoping rails. A contact pad 162 is configured to make a contact/pressure engagement with the bottom portion of the overbed table 140 with the overbed table 140 free to rise independently of the lift actuator mechanism 160. FIG. 10a showing drive motor 165, jacking rod 166 and gearbox 167.

Figure 11A:
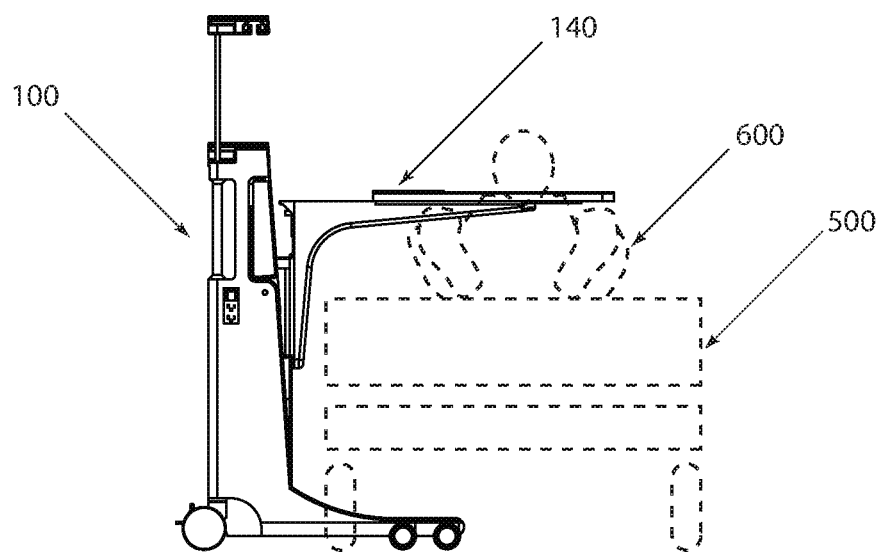
FIG. 11A is a side view of the present invention configured as an overbed table in a normal position over a patient, and, FIG. 11B is a side view of the present invention configured as an overbed table displaced by raising the patient bed.
Figure 11B:
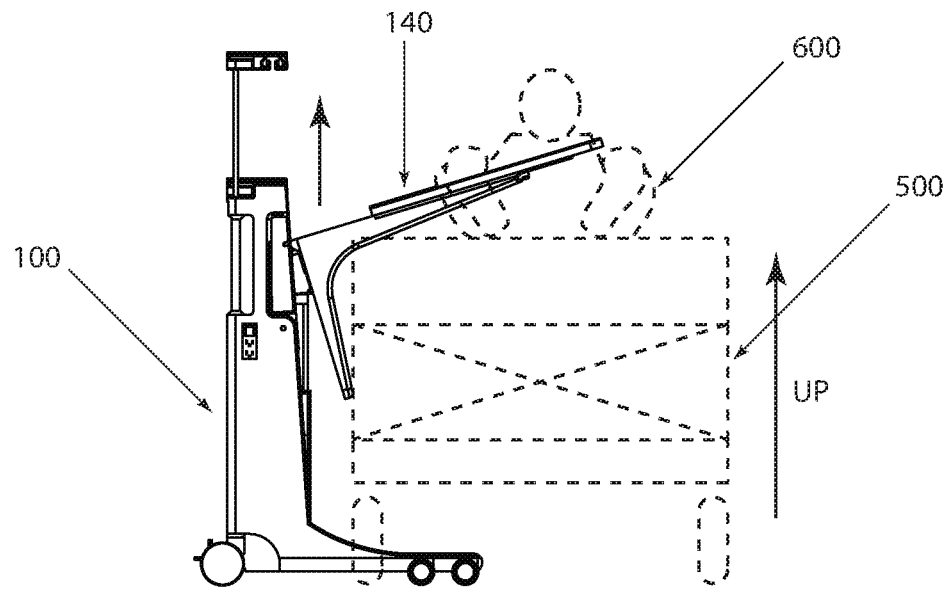

The device of the present invention or overbed table and transport chair 100 positioned over a patient 600 in bed 500 is depicted in FIG. 11a. The patient 600 has access to items placed on the table 140 and is free to change the height of the table 140 as desired. If the patient 600 chooses to raise the bed 500 independently of the table 140 there is a possibility that the patient 600 will come in contact with table 140. However, in order to avoid entrapment and possible injury to the patient 600, table 140 is free to pivot up on hinge 153 and rise vertically with the patient 600 and minimize any pressure resulting from the contract.

In view of the foregoing, those having ordinary skill in the relevant art will appreciate the advantages provided by the features of the present disclosure. It is to be understood that the above mentioned arrangements are only illustrative of the application of the principles of the present disclosure. Numerous modifications or alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. An overbed table and transport chair comprising;
   a rolling frame comprising, a rolling support base, and vertical upright members,
      the rolling support base is substantially rectangular, configured to extend under a patient bed, having a height, a width and a length wherein to provide stability and not interfere with any portion of the patient bed,
         the rolling support base having a locking caster attached at each rear corner and tandem front rollers attached proximate each front corner,
      the vertical upright members having a base end attached to the rolling support base at a rear corner of the rolling support base, each vertical upright member having a substantially uniform thickness, the back surface of each vertical upright member forming a line perpendicular to the rolling base portion,
         a cylindrical push handle formed in the upper portion of each vertical upright member,
      a seat support platform formed at the rear of the rolling support base centered between the vertical upright members,
         the seat support platform having a front surface,
         the seat support platform housing a lift actuator mechanism,
            the actuator having an operating range,
            the actuator mechanism including,
               a drive motor,
               a gearbox,
               a jacking rod and,
               a roller frame assembly extending vertically above
               the jacking rod,
               a contact pad for the jacking rod attached to the free end of the roller frame assembly and configured to move independently of the jacking rod,
   an overbed table and seat,
      the overbed table and seat having a substantially planer back surface forming a table surface, a substantially planer bottom surface extending perpendicular from the back surface, and a front surface contoured in an "L" shape forming a seat having, a back support, and a seat,
      the overbed table and seat attached to the contact pad with a hinge, and,
      the overbed table and seat configurable in two stable configurations, a first configuration wherein the back surface of the table chair portion is horizontal, forming a table, the table height infinitely adjustable within the length of the jacking rod, a second configuration wherein the overbed table and seat is rotated up past 90 degrees until bottom surface of the overbed table and seat rests on the seat support platform.

2. The overbed table and transport chair of claim 1 including a seat latch mechanism configured to secure the overbed table and seat in the second configuration.

3. The overbed table and transport chair of claim 1 including an anti-rotate mechanism configured to secure the overbed table and seat in the first configuration.

4. The overbed table and transport chair of claim 3 wherein the anti-rotate mechanism comprising,
   a t-bolt attached to the front surface of the seat support platform,
   a t-bolt slot formed in the bottom surface of the overbed table and seat,
   the t-bolt slot having an upper end and a lower end,
   the t-bolt slot including,
      a slot opening formed at the upper end of the t-bolt slot,
      an exit tilt opening formed at the lower end of the t-bolt slot,
   the t-bolt configured to insert into the slot opening when the overbed table and seat is moved into the first configuration,
   the t-bolt securely retained within the t-bolt slot when the overbed table and seat are elevated within the actuator operating range, and,
   the t-bolt configured to withdraw from the exit tilt opening if the overbed table and seat are moved above the actuator operating range.

5. The overbed table and transport chair of claim 1 including a micro-switch configured to prevent the lift actuator mechanism from operating when the overbed table and seat are in the second configuration.

6. The overbed table and transport chair of claim 1 including an IV stand formed in at least one of the vertical upright members,
   the IV stand comprising,
      an extension pole,
      a top cantilevered portion,
         the extension pole extending through the push handle, and,
         the top cantilevered portion forming the top surface of the vertical upright member.

7. The overbed table and transport chair of claim 1 wherein each vertical upright member includes a folding armrest.

8. The overbed table and transport chair of claim 1 wherein at least one vertical upright member includes an electrical/USB outlet.

9. The overbed table and transport chair of claim 1 wherein the seat support platform includes an oxygen bottle holder.

* * * * *